(12) United States Patent
Ohsu et al.

(10) Patent No.: US 8,106,020 B2
(45) Date of Patent: Jan. 31, 2012

(54) CALCIUM RECEPTOR ACTIVATOR

(75) Inventors: Takeaki Ohsu, Kawasaki (JP); Sen Takeshita, Kawasaki (JP); Yuzuru Eto, Kawasaki (JP); Yusuke Amino, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 575 days.

(21) Appl. No.: 12/117,041

(22) Filed: May 8, 2008

(65) Prior Publication Data

US 2009/0239808 A1 Sep. 24, 2009

Related U.S. Application Data

(63) Continuation of application No. PCT/JP2006/322684, filed on Nov. 8, 2006.

(60) Provisional application No. 60/738,560, filed on Nov. 22, 2005.

(30) Foreign Application Priority Data

Nov. 9, 2005 (JP) ................................. 2005-325301

(51) Int. Cl.
*C07K 5/06* (2006.01)
(52) U.S. Cl. .................................................. 514/21.91
(58) Field of Classification Search .................... 514/19, 514/21.91
See application file for complete search history.

(56) References Cited

U.S. PATENT DOCUMENTS

| | | | |
|---|---|---|---|
| 3,331,828 A * | 7/1967 | Inamine et al. | 530/332 |
| 4,741,914 A | 5/1988 | Kimizuka et al. | |
| 4,758,551 A | 7/1988 | Meister et al. | |
| 4,927,808 A * | 5/1990 | Kitahara et al. | 514/19 |
| 5,089,476 A * | 2/1992 | Agouridas et al. | 514/18 |
| 5,409,904 A | 4/1995 | Hecht et al. | |
| 5,679,397 A | 10/1997 | Kuroda et al. | |
| 6,573,299 B1 | 6/2003 | Petrus | |
| 6,716,461 B2 | 4/2004 | Miwa et al. | |
| 6,733,797 B1 | 5/2004 | Summers | |
| 7,118,775 B2 | 10/2006 | Kohmura et al. | |
| 2002/0061358 A1 | 5/2002 | Miwa et al. | |
| 2002/0176900 A1 | 11/2002 | Yegorova | |
| 2003/0211172 A1 | 11/2003 | Jones et al. | |
| 2004/0052920 A1 | 3/2004 | Koike et al. | |
| 2004/0116345 A1 | 6/2004 | Besman et al. | |
| 2004/0265471 A1 | 12/2004 | Kohmura et al. | |
| 2005/0244512 A1 | 11/2005 | Holekamp et al. | |
| 2006/0083847 A1 | 4/2006 | Iwasaki et al. | |
| 2006/0287390 A1 | 12/2006 | Sagawa et al. | |
| 2009/0130282 A1 | 5/2009 | Hofmann et al. | |
| 2009/0239310 A1 | 9/2009 | Ohsu et al. | |
| 2009/0239808 A1 | 9/2009 | Ohsu et al. | |
| 2009/0246835 A1 | 10/2009 | Iwatani et al. | |
| 2010/0105864 A1 | 4/2010 | Yoneda et al. | |
| 2010/0120698 A1 | 5/2010 | Nagasaki et al. | |
| 2010/0136197 A1 | 6/2010 | Eto et al. | |
| 2010/0183792 A1 | 7/2010 | Nagasaki et al. | |
| 2011/0046046 A1 | 2/2011 | Hara et al. | |
| 2011/0070270 A1 | 3/2011 | Kodera et al. | |
| 2011/0071075 A1 | 3/2011 | Takeuchi et al. | |

FOREIGN PATENT DOCUMENTS

| | | |
|---|---|---|
| EP | 0449354 | 10/1991 |
| EP | 0 672 354 | 9/1995 |
| EP | 1197152 | 4/2002 |
| EP | 1 554 939 | 7/2005 |
| WO | WO 92/07267 | 4/1992 |
| WO | WO94/22438 | 10/1994 |
| WO | WO 94/22438 | 10/1994 |
| WO | WO02/49653 | 6/2002 |
| WO | WO03/029417 | 4/2003 |
| WO | WO03/049687 | 6/2003 |
| WO | WO2007/042288 | 4/2007 |
| WO | WO 2007/055388 | 5/2007 |
| WO | WO2007/055393 | 5/2007 |

OTHER PUBLICATIONS

Li, Xiaoying, Neurochemistry International 29(2), 121-128, 1996.*
Li, Xiaoying, Brain Research 815(1), 81-88, 1999.*
Goodman and Gilman's Manual of Pharmacology and Therapeutics pp. 528-543 and 1059-1074 (McGraw-Hill, 2008).*
English abstract of Susumu, Kiyohara, JP 2008-054507, Mar. 2008.*
English abstract of Yuji, Uzuhashi, JP 2006-180792, Jul. 2006.*
English abstract of Mayumi, Nishimura, JP 2006-158232, Jun. 2006.*
English abstract of Yuuki, Nishimori, JP 2005-046109, Feb. 2005.*
Cobb, M. H., et al., "Structural and Conformational Properties of Peptides Interacting with the Glutathione Receptor of Hydra," Mol. Pharmacol. 1982;21:629-636.
Conigrave, A.D., et al., "L-Amino acid sensing by the calcium-sensing receptor: a general mechanism for coupling protein and calcium metabolism?" Eur. J. Clin. Nutr. 2002;56:1072-1080.
Conigrave, A. D., et at., "L-Amino acid sensing by the extracellular $Ca^{2+}$-sensing receptor," PNAS 2000;97(9):4814-4819.
Database CA [online], Chemical Abstracts Service, Columbus, OH, US; May 12, 1984, Valyakina, T. I., et al.; Biological activity of peptide and depsipeptide analogs of ophthalmic [.gamma.-glutamyl-.alpha.-aminobutyrylglycine] and norophthalmic [.gamma.-glutamyl-alanylglycine] acids in glyoxalase I and formaldehyde: NAD-oxidoreductase enzyme systems; XP-002438771, 1 pg.
De Craecker, S., et al., "Characterization of the peptide substrate specificity of glutathionylspermidine synthetase from *Crithidia fasciculate*," Mol. Biochem. Parasitol. 1997;84:25-32.

(Continued)

Primary Examiner — David Lukton
(74) Attorney, Agent, or Firm — Shelly Guest Cermak; Cermak Nakajima LLP

(57) ABSTRACT

A calcium receptor activator and compositions containing at least one of the following: γ-Glu-Cys-Gly, γ-Glu-Cys(SNO)-Gly, γ-Glu-Ala, γ-Glu-Gly, γ-Glu-Cys, γ-Glu-Met, γ-Glu-Thr, γ-Glu-Val, γ-Glu-Orn, Asp-Gly, Cys-Gly, Cys-Met, Glu-Cys, Gly-Cys, Leu-Asp, D-Cys, γ-Glu-Met(O), γ-Glu-Val-Val, γ-Glu-Val-Glu, γ-Glu-Val-Lys, γ-Glu-γ-Glu-Val, γ-Glu-Val-NH₂, γ-Glu-Val-ol, γ-Glu-Ser, γ-Glu-Tau, γ-Glu-Cys(S-Me)(O), γ-Glu-Leu, γ-Glu-Ile, γ-Glu-t-Leu, γ-Glu-Cys(S-allyl)-Gly, γ-Glu-Gly-Gly, γ-Glu-Val-Phe, γ-Glu-Val-Ser, γ-Glu-Val-Pro, γ-Glu-Val-Arg, γ-Glu-Val-Asp, γ-Glu-Val-Met, γ-Glu-Val-Thr, γ-Glu-Val-His, γ-Glu-Val-Asn, γ-Glu-Val-Gln, γ-Glu-Val-Cys, γ-Glu-Val-Orn, γ-Glu-Ser-Gly, γ-Glu-Cys(S-Me), γ-Glu-Abu-Gly, γ-Glu-Cys(S-Me)-Gly, and γ-Glu-Val-Gly.

4 Claims, 4 Drawing Sheets

OTHER PUBLICATIONS

Leslie, E. M., et al., "Structural Requirements for Functional Interaction of Glutathione Tripeptide Analogs with the Human Multidrug Resistance Protein I (MRP1)," J. Pharmacol. Exper. Ther. 2003;304(2):643-652.

Wang, M., et al., "Activation of Family C G-protein-coupled Receptors by the Tripeptide Glutathione," J. Biol. Chem. 2006;281(13):8864-8870.

International Search Report and Written Opinion of the International Searching Authority for PCT/JP2006/322684 (Jul. 13, 2007).

Bevilacqua, M., et al., "Increased Gastrin and Calcitonin Secretion after Oral Calcium or Peptones Administration in Patents with Hypercalciuria: A Clue to an Alteration in Calcium-Sensing Receptor Activity," J. Clin. Endocrinol. Metab. 2005;90(3):1489-1494.

Breitwieser, G. E., et al., "Calcium sensing receptors as integrators of multiple metabolic signals," Cell Calcium 2004;35:209-216.

Brown, E. M., et al., "Cloning and characterization of an extracellular $Ca^{2+}$-sensing receptor from bovine parathyroid," Nature 1993;366:575-580.

Canaff, L., et al., "Extracellular Calcium-sensing Receptor Is Expressed in Rat Hepatocytes," J. Biol. Chem. 2001;276(6):4070-4079.

Chattopadhyay, N., et al., "Expression of Extracellular Calcium-Sensing Receptor by Human Lens Epithelial Cells," Biochem. Biophys. Res. Comm. 1997;233:801-805.

Chattopadhyay, N., et al., "Mitogenic Action of Calcium-Sensing Receptor on Rat Calvarial Osteoblasts," Endocrinology 2004;145(7):3451-3462.

Cheng, I., et al., "Identification and Localization of the Extracellular Calcium-Sensing Receptor in Human Breast," J. Clin. Endocrinol. Metab. 1998;83(2):703-707.

Cheng, S. X., et al., "Expression of calcium-sensing receptor in rat colonic epithelium: evidence for modulation of fluid secretion," Am. J. Physiol. Gastrointest. Liver Physiol. 2002;283:240-250.

Cifuentes, M., et al., "Calcium-Sensing Receptor Expression in Human Adipocytes," Endocrinology 2005;146(5):2176-2179.

House, M. G., et al., "Expression of an Extracellular Calcium-Sensing Receptor in Human and Mouse Bone Marrow Cells," J. Bone Mm. Res. 1997;12(12):1959-1970.

Jensen, B., et al., "High extracellular calcium attenuates adipogenesis in 3T3-L1 preadipocytes," Exp. Cell Res. 2004;301:280-292.

Malaisse, W. J., et al., "Possible Participation of an Islet B-Cell Calcium-Sensing Receptor in Insulin Release," Endocrine 1999;11(3):293-300.

McLARNON, S. J., et al., "Physiological and pharmacological agonists of the extracellular $Ca^{2+}$-sensing receptor," Eur. J. Phamicol. 2002;447:271-278.

Nemeth, E. F., et al., "Calcimimetics with potent and selective activity on the parathyroid calcium receptor," Proc. Natl. Acad. Sci. USA 1998;95:4040-4045.

Olszak, I. T., et al., "Extracellular calcium elicits a chemokinetic response from monocytes in vitro and in vivo," J. Clin. Investigation 2000;105(9):1299-1299-1305.

Squires, P. E., "Non-$Ca^{2+}$-horneostatie functions of the extracellular $Ca^{2+}$-sensing receptor (CaR) in endocrine tissues," J. Endocrinol. 2000;165:173-177.

Tu, Chia-Ling, et al, "The role of the calcium-sensing receptor in epidermal differentiation," Cell Calcium 2004;35:265-273.

Yamauchi, M., et al., "Involvement of calium-sensing receptor in osteoblastic differentiation of mouse MC3T3-E1 cells," Am. J. Physiol. Endocrinol. Metab. 2004;288:E608-E616.

International Preliminary Report on Patentability for PCT Patent App. No. PCT/JP2006/322684 (May 22, 2008).

Anonymous: "Calcium sensing receptor," Wikipedia (English language), Aug. 27, 2010, XP002598415, Retrieved from the Internet: URL: http://en.wikipedia.org/wiki/Calcium-sensing_receptor.

European Search Report for EP Patent App. No. 10002380.3 (Sep. 17, 2010).

International Search Report and Written Opinion of the International Searching Authority for PCT Patent App. No. PCT/JP2006/322694 (Mar. 16, 2007).

Ueda, Y., et al., "Characteristic Flavor Constituents in Water Extract of Garlic," Agric. Biol. Chem. 1990;54(1):163-169.

Ueda, Y., et al., "Composition of Sulfur-Containing Components in Onion and Their Flavor Characters," Biosci. Biotech. Biochem. 1994;58(1):108-110.

Valyakina, T. I., et al., "Biological activity of peptide and depsipeptide analogs of ophthalmic [Y-glutamyl-α-aminobutyrylglycine] and norophthalmic [Y-glutamyl-alanylglycine] acids in glyoxalase I and formaldehyde: NAD-oxidoreductase enzyme systems," Biokhimiya 1972;37(4):757-761, with English abstract.

International Search Report and Written Opinion of the International Searching Authority for PCT Patent App. No. PCT/JP2006/322694 (Mar. 16, 2007).

Morrot, G., et al., "The Color of Odors," Brain and Language 2001;79:309-320.

Dunkel, A., et al., "Molecular and Sensory Characterization of γ-Glutamyl Peptides as Key Contributors to the Kokumi Taste of Edible Beans (Phaseolus vulgaris L.)," J. Agric. Food Chem. 2007;55:6712-6719.

Ueda, Y., et al., "Flavor Characteristics of Glutathione in Raw and Cooked Foodstuffs," Biosci. Biotech. Biochem. 1997;61(12):1977-1980.

International Search Report for PCT Patent App. No. PCT/JP2008/058325 (May 27, 2008).

International Preliminary Report on Patentability for PCT Patent App. No. PCT/JP2008/058325 (Dec. 3, 2009).

Suzuki, H., et al., "Improvement of the Flavor of Amino Acids and Peptides Using Bacterial γ-Glutamyltranspeptidase," Recents Highlight in Flavor Chemistry & Biology 2007, pp. 227-232, Eds. Hofmann, T., et al., Deutsche Forschungsanstalt für Lebensmittelchemie, Garching, Germany.

Supplementary European Search Report for EP Patent App. No. 08752255.3 (Oct. 27, 2010).

Notice of Reason for Rejection in Japanese Patent App. No. 2010-034162 (Jan. 25, 2011) with English translation thereof.

Office Action issued in U.S. Appl. No. 12/117,027 (Jan. 4, 2011).

Abdulrahim Jayyab, Nutritional Pharmacology of Glutathione, www.naturalhealthweb.com/article/Jayyab.7.html, Self Improvement Online, Inc. 2003, p. 1-2.

Ueda, Y. et al., "Glutathione in raw and Cooked Foodstuffs," Biosci. Biotech. Biochem. 1997;61(12):1977-1980.

Danner, J., et al., "Interaction of Glutathione Analogues with Hydra attenuata γ-Glutamyltransferase," Biochem. J. 1978;175:547-553.

English abstract of Makoto, et al., JP 60-009465, Jan., 1985.

English abstract of Kouji, et al., JP 08-289760, Nov., 1996.

English abstract of Hiroshi, et al., JP 10-276709, Oct., 1998.

Shchukina, L. A., et al., "Synthesis and biological activity of glycolyl 3-glutathione," Inst. Khim. Prirod. Soed., Moscow, USSR, Zhurnal Obshchei Khimii (1967), 37(9), 1980-1987. (Abstract only).

English abstract of Takahiro, et al., JP 2004-215563, Aug., 2004.

English abstract of Takahiro, et al., JP 2004-267160, Sep., 2004.

English abstract and partial English translation (claim 1 and examples 1-4) of Kenichi, et al., JP 60-232071, Nov., 1985.

English abstract of Noriko et al., Dec., 2002., JP 2002-36953.

Leslie, E. M., et al., "Structural Requirements for Functional Interaction of Glutathione Tripeptide Analogs with the Human Multidrug Resistance Protein 1 (MRP1)," J. Pharmacol. Exper. Ther. 2003;304(2):643-653.

* cited by examiner

SEQUENCE LISTING

```
<160> NUMBER OF SEQ ID NOS: 4

<210> SEQ ID NO 1
<211> LENGTH: 49
<212> TYPE: DNA
<213> ORGANISM: Artificial
<220> FEATURE:
<223> OTHER INFORMATION: hCASR_N primer

<400> SEQUENCE: 1
actaatacga ctcactatag ggaccatggc attttatagc tgctgctgg                49

<210> SEQ ID NO 2
<211> LENGTH: 29
<212> TYPE: DNA
<213> ORGANISM: Artificial
<220> FEATURE:
<223> OTHER INFORMATION: hCASR_C primer
```

```
<400> SEQUENCE: 2
ttatgaattc actacgtttt ctgtaacag                                         29

<210> SEQ ID NO 3
<211> LENGTH: 23
<212> TYPE: DNA
<213> ORGANISM: Artificial
<220> FEATURE:
<223> OTHER INFORMATION: rCASR_f primer

<400> SEQUENCE: 3
atggaaagct cagatgaaat gtc                                               23

<210> SEQ ID NO 4
<211> LENGTH: 24
<212> TYPE: DNA
<213> ORGANISM: Artificial
<220> FEATURE:
<223> OTHER INFORMATION: rCASR_r primer

<400> SEQUENCE: 4
ggagtgtaat acgttttccg tcac                                              24
```

CALCIUM RECEPTOR ACTIVATOR

This application is a continuation under 35 U.S.C. §120 to PCT Patent Application No, PCT/JP2006/322684, filed Nov. 8, 2006, which claims priority under 35 U.S.C. §119 to Japanese Patent Application No. 2005-325301, filed on Nov. 9, 2005, and U.S. Provisional Patent Application No. 60/738,560, filed on Nov. 22, 2005, all of which are hereby incorporated by reference in their entireties. Also, the Sequence Listing filed electronically herewith is hereby incorporated by reference (File name: US-260_Seq_List_Copy__1; File size: 1 KB; Date recorded: May 8, 2008).

BACKGROUND OF THE INVENTION

1. Field of the Invention

The present invention relates to a calcium receptor activator containing D-Cys or a peptide, a pharmaceutical composition containing the calcium receptor activator as the active ingredient, and a method for screening for a calcium receptor activation inhibitor using the calcium receptor activator.

2. Brief Description of the Related Art

The calcium receptor (also called the calcium sensing receptor CaSR) contains 1078 amino acids, and is classified in class C of the seven-transmembrane receptors (G protein-coupled receptor; GPCR). The cloning of the gene for the calcium receptor was reported in 1993 (Nature, 1993 Dec. 9, 366(6455):575-80). The calcium receptor is known to cause various cellular responses through elevation of intracellular the calcium levels etc., when it is activated with calcium etc. The sequence of the human calcium receptor gene is registered with GenBank (Accession No. NM_000388), and is well conserved among many animal species.

The calcium receptor may promote or suppress various biological functions. Therefore, therapeutic agents which act as activators or inhibitors of the calcium receptor are appropriately used in the treatment of neurological diseases, hepatic diseases, cardiovascular diseases, digestive system diseases, and other diseases, depending on the pathological conditions. For example, the calcium receptor is able to detect increased levels of blood calcium in the parathyroid, and suppress secretion of the parathyroid hormone (PTH) to correct the blood calcium level. Therefore, reduction of the blood calcium level is an expected effect of administration of a calcium receptor activator. It has been reported that when a calcium receptor activator is used to treat secondary hyperparathyroidism in a hemodialysis patient, the PTH level is reduced without the calcium and phosphorus levels increasing.

Since functional studies of the calcium receptor have been conducted primarily during calcium homeostasis, applications so far typically concern bone metabolic diseases in which calcium regulation is involved. However, through analysis of genetic expression, it is now known that the calcium receptor is widely distributed in living bodies in addition to its presence in the parathyroid and kidney tissues. (J. Endocrinol., 2000 May, 165(2):173-7, Eur. J. Pharmacol., 2002 Jul. 5, 447(2-3):271-8), and the possibility that the calcium receptor is involved in many various biological functions and the etiology of many diseases has been proposed. For example, the calcium receptor is thought to be involved in the functions of the liver, heart, lung, alimentary canal, lymphocyte, and pancreas. It has been confirmed that the calcium receptor is expressed in a wide range of tissues by analyses based on RT-PCR using RNAs extracted from rat tissues. Therefore, the increased importance of activators and inhibitors of the calcium receptor in various applications is becoming recognized.

Moreover, cations such as gadolinium, basic peptides such as polyarginine, polyamines such as spermine, amino acids such as phenylalanine, and so forth have been reported to be calcium receptor activators (Cell Calcium, 2004 Mar., 35(3): 209-16).

Although many specific calcium receptor activators have been developed as described above, few of these compounds are native to living bodies, and those that are native have very low activities. Therefore, therapeutic agents containing these activators pose serious problems including side effects, permeability, and sufficient activity. For example, although it is known that amino acids act on calcium receptors, their use as calcium receptor activators is usually unsuccessful due to their very weak activity. Moreover, although macromolecules such as polyarginine have been reported to be an activator as described above, the activator function is based on their actions as polyvalent cations, which have irregular structures. That is, peptides having a specific structure are not known to be useful as a calcium receptor activator.

SUMMARY OF THE INVENTION

An aspect of the present invention is to provide a highly active calcium receptor activator which is very safe for administration to living bodies. Another aspect of the present invention is to provide a method of screening for a calcium receptor activation inhibitor.

Activators of the calcium receptor were searched for, and as a result, it was found that low molecular peptides, including glutathione, were able to activate the calcium receptor. The present invention provides the following:

It is an aspect of the present invention to provide a calcium receptor activator selected from the group consisting of γ-Glu-Cys-Gly, γ-Glu-Cys(SNO)-Gly, γ-Glu-Ala, γ-Glu-Gly, γ-Glu-Cys, γ-Glu-Met, γ-Glu-Thr, γ-Glu-Val, γ-Glu-Orn, Asp-Gly, Cys-Gly, Cys-Met, Glu-Cys, Gly-Cys, Leu-Asp, D-Cys, γ-Glu-Met(O), γ-Glu-Val-Val, γ-Glu-Val-Glu, γ-Glu-Val-Lys, γ-Glu-γ-Glu-Val, γ-Glu-Val-$NH_2$, γ-Glu-Val-ol, γ-Glu-Ser, γ-Glu-Tau, γ-Glu-Cys(S-Me)(O), γ-Glu-Leu, γ-Glu-Ile, γ-Glu-t-Leu, γ-Glu-Cys(S-allyl)-Gly, γ-Glu-Gly-Gly, γ-Glu-Val-Phe, γ-Glu-Val-Ser, γ-Glu-Val-Pro, γ-Glu-Val-Arg, γ-Glu-Val-Asp, γ-Glu-Val-Met, γ-Glu-Val-Thr, γ-Glu-Val-His, γ-Glu-Val-Asn, γ-Glu-Val-Gln, γ-Glu-Val-Cys, γ-Glu-Val-Orn, γ-Glu-Ser-Gly, γ-Glu-Cys(S-Me), γ-Glu-Abu-Gly, γ-Glu-Cys(S-Me)-Gly, γ-Glu-Val-Gly, and combinations thereof.

It is a further aspect of the present invention to provide a composition comprising the calcium receptor activator as described above, and one or more other compounds having calcium receptor activation activity.

It is a further aspect of the present invention to provide the composition as described above, wherein the one or more other compounds having calcium receptor activation activity is a cation.

It is a further aspect of the present invention to provide a pharmaceutical composition comprising the calcium receptor activator as described above.

It is a further aspect of the present invention to provide a method of screening for a calcium receptor activation inhibitor, comprising using the calcium receptor activator as described above.

It is a further aspect of the present invention to provide a method for activating a calcium receptor comprising administering a substance selected from the group consisting of γ-Glu-Ala, γ-Glu-Gly, γ-Glu-Cys, γ-Glu-Met, γ-Glu-Thr, γ-Glu-Val, γ-Glu-Orn, Asp-Gly, Cys-Gly, Cys-Met, Glu-Cys, Gly-Cys, Leu-Asp, D-Cys, γ-Glu-Met(O), γ-Glu-Val-NH$_2$, γ-Glu-Val-ol, γ-Glu-Ser, γ-Glu-Tau, γ-Glu-Cys(S-Me)(O), γ-Glu-Leu, γ-Glu-Ile, γ-Glu-t-Leu, γ-Glu-Cys(S-Me), and combinations thereof to a target.

It is a further aspect of the present invention to provide a method for activating a calcium receptor comprising administering a substance selected from the group consisting of γ-Glu-Cys-Gly, γ-Glu-Cys(SNO)-Gly, γ-Glu-Val-Val, γ-Glu-Val-Glu, γ-Glu-Val-Lys, γ-Glu-γ-Glu-Val, γ-Glu-Cys(S-allyl)-Gly, γ-Glu-Gly-Gly, γ-Glu-Val-Phe, γ-Glu-Val-Ser, γ-Glu-Val-Pro, γ-Glu-Val-Arg, γ-Glu-Val-Asp, γ-Glu-Val-Met, γ-Glu-Val-Thr, γ-Glu-Val-His, γ-Glu-Val-Asn, γ-Glu-Val-Gln, γ-Glu-Val-Cys, γ-Glu-Val-Orn, γ-Glu-Ser-Gly, γ-Glu-Abu-Gly, γ-Glu-Cys(S-Me)-Gly, γ-Glu-Val-Gly, and combinations thereof.

DESCRIPTION OF THE PREFERRED EMBODIMENTS

Figure 1:
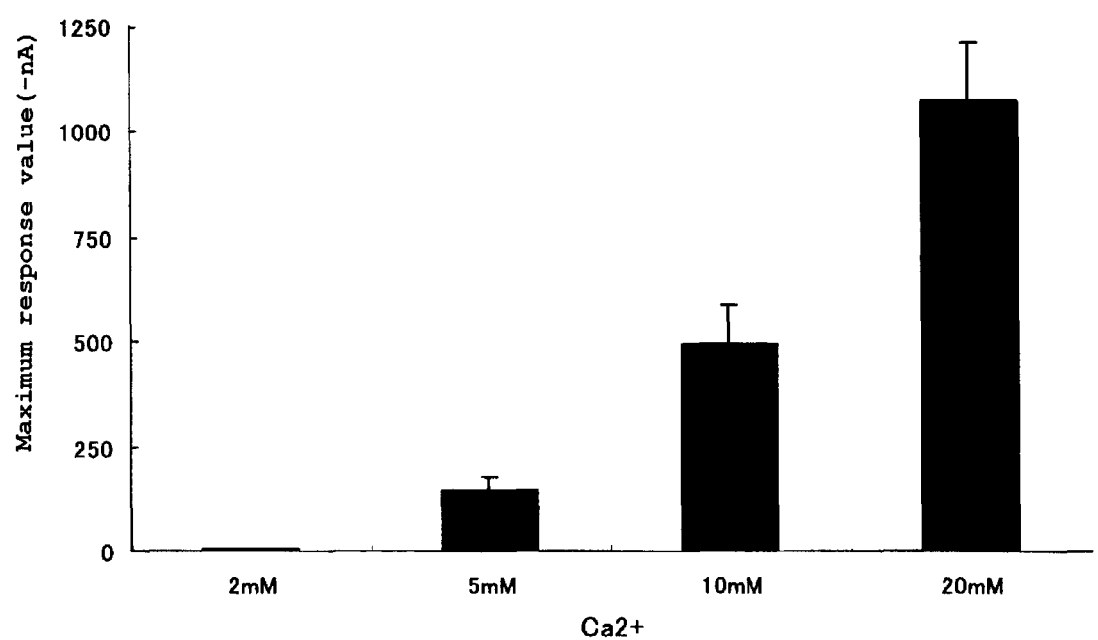
FIG. 1 shows the action of calcium on the calcium receptor. The human calcium receptor cRNA was introduced into *Xenopus laevis* oocytes by microinjection. Values of the intracellular response currents were recorded when a calcium chloride solution was added at an arbitrary concentration. The maximum values of intracellular currents were considered response current values. It was confirmed that no response was observed in control oocytes microinjected with distilled water.

Hereinafter, the present invention will be explained in detail.

A highly active calcium receptor activator which is very safe for administration to living bodies is provided. Moreover, a method for screening for a calcium receptor activation inhibitor is provided.

The calcium receptor activator or composition containing the activator of the present invention contains one or more of the following: γ-Glu-Cys-Gly, γ-Glu-Cys(SNO)-Gly, γ-Glu-Ala, γ-Glu-Gly, γ-Glu-Cys, γ-Glu-Met, γ-Glu-Thr, γ-Glu-Val, γ-Glu-Orn, Asp-Gly, Cys-Gly, Cys-Met, Glu-Cys, Gly-Cys, Leu-Asp, D-Cys, γ-Glu-Met(O), γ-Glu-Val-Val, γ-Glu-Val-Glu, γ-Glu-Val-Lys, γ-Glu-γ-Glu-Val, γ-Glu-Val-NH$_2$, γ-Glu-Val-ol, γ-Glu-Ser, γ-Glu-Tau, γ-Glu-Cys(S-Me)(O), γ-Glu-Leu, γ-Glu-Ile, γ-Glu-t-Leu, γ-Glu-Cys(S-allyl)-Gly, γ-Glu-Gly-Gly, γ-Glu-Val-Phe, γ-Glu-Val-Ser, γ-Glu-Val-Pro, γ-Glu-Val-Arg, γ-Glu-Val-Asp, γ-Glu-Val-Met, γ-Glu-Val-Thr, γ-Glu-Val-His, γ-Glu-Val-Asn, γ-Glu-Val-Gln, γ-Glu-Val-Cys, γ-Glu-Val-Orn, γ-Glu-Ser-Gly, γ-Glu-Cys(S-Me), γ-Glu-Abu-Gly, γ-Glu-Cys(S-Me)-Gly, and γ-Glu-Val-Gly. All the amino acids and amino acid residues in these peptides are L-isomers, unless otherwise specified.

In the present specification, abbreviations for amino acid residues are as follows:
(1) Gly: Glycine
(2) Ala: Alanine
(3) Val: Valine
(4) Leu: Leucine
(5) Ile: Isoleucine
(6) Met: Methionine
(7) Phe: Phenylalanine
(8) Tyr: Tyrosine
(9) Trp: Tryptophan
(10) His: Histidine
(11) Lys: Lysine
(12) Arg: Arginine
(13) Ser: Serine
(14) Thr: Threonine
(15) Asp: Aspartic acid
(16) Glu: Glutamic acid
(17) Asn: Asparagine
(18) Gln: Glutamine
(19) Cys: Cysteine
(20) Pro: Proline
(21) Orn: Ornithine
(22) Sar: Sarcosine
(23) Cit: Citruline
(24) N-Val: Norvaline
(25) N-Leu: Norleucine
(26) Abu: alpha-Aminobutylic acid
(27) Tau: Taurine
(28) Hyp: Hydroxyproline
(29) t-Leu: tert-Leucine
(30) Cys (S-Me): S-methyl cysteine
(31) Cys (S-allyl): S-allyl cysteine
(32) Val-NH$_2$: valinamide
(33) Val-ol: valinol (2-amino-3-methyl-1-butanol)

The "O" in the formulas γ-Glu-Met(O) and γ-Glu-Cys(S-Me)(O) indicates a sulfoxide structure. The "γ" in γ-Glu indicates that glutamic acid bonds to another amino acid via the γ position of the carboxy group in the glutamic acid. γ-Glu-Cys(SNO)-Gly has the following structural formula:

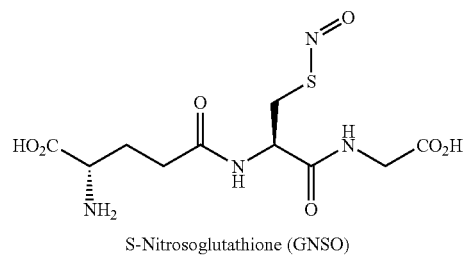

S-Nitrosoglutathione (GNSO)

The calcium receptor is also called the calcium sensing receptor (CaSR), and belongs to class C of the seven-transmembrane receptors. The "calcium receptor activator" is a substance that acts on the calcium receptor to activate the calcium receptor and control the functions of cells in which the calcium receptor is expressed. Furthermore, the phrase "to activate the calcium receptor" indicates when a ligand (activator) binds to the calcium receptor, resulting in activation of the guanine nucleotide binding protein, which thereby transmits signals.

The following substances are able to activate the calcium receptor and can be used as calcium receptor activators or in compositions to be used as calcium receptor activators: γ-Glu-Cys-Gly, γ-Glu-Cys(SNO)-Gly, γ-Glu-Ala, γ-Glu-Gly, γ-Glu-Cys, γ-Glu-Met, γ-Glu-Thr, γ-Glu-Val, γ-Glu-Orn, Asp-Gly, Cys-Gly, Cys-Met, Glu-Cys, Gly-Cys, Leu-Asp, D-Cys, γ-Glu-Met(O), γ-Glu-Val-Val, γ-Glu-Val-Glu, γ-Glu-Val-Lys, γ-Glu-γ-Glu-Val, γ-Glu-Val-NH$_2$, γ-Glu-Val-ol, γ-Glu-Ser, γ-Glu-Tau, γ-Glu-Cys(S-Me)(O), γ-Glu-Leu, γ-Glu-Ile, γ-Glu-t-Leu, γ-Glu-Cys(S-allyl)-Gly, γ-Glu-Gly-Gly, γ-Glu-Val-Phe, γ-Glu-Val-Ser, γ-Glu-Val-Pro, γ-Glu-Val-Arg, γ-Glu-Val-Asp, γ-Glu-Val-Met, γ-Glu-Val-Thr, γ-Glu-Val-His, γ-Glu-Val-Asn, γ-Glu-Val-Gln, γ-Glu-Val-Cys, γ-Glu-Val-Orn, γ-Glu-Ser-Gly, γ-Glu-Cys(S-Me), γ-Glu-Abu-Gly, γ-Glu-Cys(S-Me)-Gly, and γ-Glu-Val-Gly. These activators may be used independently, or two or more can be used as a mixture.

Commercially available peptides and amino acids, if available can be used in the methods and compositions described herein. Furthermore, the peptides can be obtained by using a known technique such as chemical synthesis, or synthesis via an enzymatic reaction. Chemical synthesis is convenient since the number of amino acid residues of the peptides is small, for example, 2 or 3 residues. A peptide synthesizer can be used when chemically synthesizing the peptides, either partially or entirely. Examples of such methods include, for example, a peptide solid phase synthetic method. Peptides synthesized as described above can be purified by usual means, for example, ion exchange chromatography, reversed phase high performance liquid chromatography, affinity chromatography, and so forth. These peptide solid phase synthetic methods and the following peptide purification are well known in this technical field.

Furthermore, the peptides can also be prepared by an enzymatic reaction. For example, the method described in International Patent Publication WO2004/011653 can be used. That is, one amino acid or dipeptide with an esterified or amidated carboxyl terminus can be reacted with an amino acid having a free amino group, for example, an amino acid with a protected carboxyl group, in the presence of a peptide producing enzyme, and purifying the produced dipeptide or tripeptide. Examples of the peptide producing enzyme include a culture of microorganisms having an ability to produce peptides, microbial cells separated from such culture, processed products of these cells, peptide producing enzymes derived from such microorganisms, and so forth.

Salt forms of the peptides and amino acids are also included. Pharmacologically acceptable salts of the peptides and amino acids may be used. Examples of salts containing an acidic group such as a carboxyl group include ammonium salts, salts with alkali metals such as sodium and potassium, salts with alkaline earth metals such as calcium, and magnesium, aluminum salts, zinc salts, salts with organic amines such as triethylamine, ethanolamine, morpholine, pyrrolidine, piperidine, piperazine, and dicyclohexylamine, and salts with basic amino acids such as arginine and lysine. Examples of salts with a basic group include salts with inorganic acids such as hydrochloric acid, sulfuric acid, phosphoric acid, nitric acid, and hydrobromic acid, salts with organic carboxylic acids such as acetic acid, citric acid, benzoic acid, maleic acid, fumaric acid, tartaric acid, succinic acid, tannic acid, butyric acid, hibenzoic acid, pamoic acid, enanthoic acid, decanoic acid, teoclic acid, salicylic acid, lactic acid, oxalic acid, mandelic acid, and malic acid, and salts with organic sulfonic acids such as methanesulfonic acid, benzenesulfonic acid, and p-toluenesulfonic acid.

The human calcium receptor encoded by the human calcium receptor gene (GenBank Accession No. NM_000388) is preferred. However, the chosen calcium receptor is not limited to the protein encoded by the gene of the aforementioned reported GenBank sequence, but it may also be a protein encoded by a gene having a homology of 60% or more, preferably 80% or more, more preferably 90% or more, to the aforementioned sequence, so long as the protein functions as a calcium receptor. The GPRC6A receptor and the 5.24 receptor are also known to be subtypes of the calcium receptor, and they can also be used in the methods described herein. The calcium receptor function can be examined by expressing a gene of interest in a cell and measuring changes in the electric current, or intracellular calcium ion concentration at the time of the addition of calcium.

The calcium receptor activator may be a substance that activates any calcium receptor, regardless of origin, and may activate a calcium receptor derived from animals such as mouse, rat, and dog.

The calcium receptor activation activity of the peptides and amino acids can be confirmed by using live cells which express a calcium receptor or a fragment thereof, cell membranes which express a calcium receptor or a fragment thereof, an in vitro system containing a calcium receptor or a fragment thereof, or the like.

An example using live cells is shown below. However, methods for confirming calcium receptor activity is not limited to this example.

A calcium receptor can be expressed in cultured cells such as *Xenopus laevis* oocytes, hamster ovarian cells, and human fetal kidney cells. The calcium receptor can be expressed by cloning a calcium receptor gene in a plasmid that contains a foreign gene and introducing the plasmid or cRNA obtained by using the plasmid as a template. To detect the reaction, electrophysiological techniques, fluorescent indicator reagents that indicate an increase in intracellular calcium level, and so forth, can be used.

Expression of the calcium receptor is first confirmed based on the response to calcium or a specific activator. Oocytes can be used that have an intracellular current with calcium at a concentration of about 5 mM, or cultured cells can be used that show fluorescence of the fluorescent indicator reagent with calcium at a concentration of about 5 mM. Calcium concentration dependency is determined by changing the calcium concentration. Then, a test substance such as a peptide is prepared to a concentration of about 1 μM to 1 mM, and added to the oocytes or cultured cells, and whether the aforementioned peptide or the like functions as an activator for the calcium receptor is determined.

Furthermore, the calcium receptor activator compositions of the present invention may further contain one or more other compounds which also have calcium receptor activation activity, in addition to the activators named above.

Examples of known compounds having calcium receptor activation activity include, but are not limited to, cations such as calcium and gadolinium, basic peptides such as polyarginine and polylysine, polyamines such as putrescine, spermine and spermidine, proteins such as protamine, amino acids such as phenylalanine, cinacalcet, and so forth. These compounds may be added to the activator composition alone, or as a mixture of two or more. Cations such as calcium and gadolinium are preferred, and the calcium cation is more preferred. That is, it is preferred that at least one of the known calcium receptor activators that is further added is a cation.

By combining known calcium receptor activator compounds with the peptides and amino acids described herein, stronger activation of the calcium receptor can be obtained. The ratio of the total amount of the peptides and amino acids described herein to the total amount of the known calcium receptor activator compounds is not particularly limited, so long as stronger activation of the calcium receptor is obtained. However, for example, the mass ratio of the total amount of the peptides and amino acids described herein to the total amount of the known calcium receptor activator compounds is preferably 1:00 to 100:1.

The calcium receptor is expressed in various tissues and is responsible for various physiological functions. Moreover, activators of the calcium receptor have been developed as therapeutic drugs to treat medical diseases (for example, Therapeutic drugs of hypercalcemia, Proc. Natl. Acad. Sci. USA, 1998 Mar. 31, 95(7):4040-5).

Other than controlling calcium levels, it has been reported, for example, that the calcium receptor is expressed in both mature and undifferentiated adipocytes, and is involved in the suppression of differentiation (Endocrinology, 2005 May, 146(5):2176-9; Exp. Cell Res., 2004 December, 10; 301(2): 280-92). In bone marrow cells, it is expressed in erythroblasts, megakaryocytes, and thrombocytes, and is involved in hematogenous regulation (J. Bone Miner Res., 1997 December, 12 (12):1959-70). The calcium receptor is also expressed in gastric parietal cells and is involved in gastric acid secretion (J. Clin. Endocrinol. Metab., 2005 March, 90(3):1489-94). In addition to the above, it has been suggested that it is expressed in the duodenum, jejunum, ileum (Am. J. Physiol. Gastrointest. Liver Physiol., 2002 July, 283(1):G240-50), large intestine (Am. J. Physiol. Gastrointest. Liver Physiol., 2002 July, 283(1):G240-50), epidermal keratinocytes (Cell Calcium, 2004 March, 35(3):265-73), hepatic cells (J. Biol. Chem., 2001 Feb. 9, 276(6):4070-9), vortex lentis (Biochem. Biophys. Res. Commun., 1997 Apr. 28, 233(3):801-5), Langerhans' islets in the pancreas (Endocrine., 1999 December, 11(3):293-300), lung (J. Clin. Endocrinol. Metab., 1998 February, 83(2):703-7), monocyte type cells (J. Clin. Invest., 2000 May, 105(9):1299-305), osteoblasts (Endocrinology, 2004 July, 145(7):3451-62; Am. J. Physiol. Endocrinol. Metab., 2005 March, 288(3):E608-16, Epub. 2004 Nov. 16), and so forth, and is involved in the functional regulation of these tissues.

Therefore, the calcium receptor activator and compositions containing the activator can be used as an active ingredient in a pharmaceutical composition for preventing or treating a disease in which the calcium receptor is involved. Examples of diseases in which the calcium receptor is involved include medical diseases, surgical diseases, pediatric diseases, orthopedic diseases, plastic surgery diseases, neurosurgical diseases, dermatological diseases, urological diseases, obstetric or gynecological diseases, ophthalmologic diseases, otorhinolaryngological diseases, dentistry or oral surgery diseases, and so forth.

The method for administering a pharmaceutical composition containing a calcium receptor activator is not particularly limited, and may include oral administration, invasive administration utilizing injection or the like, administration via suppositories, or transdermal administration. The active ingredient, for example, the calcium receptor activator, can be mixed with a non-toxic pharmaceutical carrier in the form of solid or liquid suitable for any of these administration methods, and may be prepared by any conventional pharmaceutical methods. Examples of pharmaceutical compositions include, for example, solid preparations such as tablets, granules, powders, and capsules, liquid preparations such as solutions, suspensions, and emulsions, lyophilized preparations, and so forth. These preparations can be prepared by conventional means typically used for the preparation of drugs.

Examples of non-toxic pharmaceutical carriers include, for example, glucose, lactose, sucrose, starch, mannitol, dextrin, aliphatic acid glycerides, polyethylene glycol, hydroxyethyl-starch, ethylene glycol, polyoxyethylene sorbitan fatty acid esters, gelatin, albumin, amino acids, water, physiological saline, and so forth. Moreover, conventional additives such as stabilizers, wetting agents, emulsifiers, binders, and isotonic agents can also be optionally added as required.

The dose of the pharmaceutical composition may be that which is effective for a therapeutic and prophylactic treatment, and can be suitably adjusted depending on age, sex, weight, symptoms, and so forth of the patient. However, for oral administration, for example, it is preferably 0.01 to 10 g, more preferably 0.1 to 1 g, in terms of the total amount of the peptides and amino acids employed as the calcium receptor activator, per 1 kg of body weight for a single administration. Frequency of the administration is not particularly limited, and it can be administered once to several times per day.

The calcium receptor activator can also be used as a food or drink, or as a component of a food or drink, which is effective for treatment or prevention of a disease in which the calcium receptor is involved. For example, it can be prepared as a food or drink, or as a component of a food or drink, which indicates that it has a curative or preventive effect for such diseases on the container or package containing the food or drink.

The calcium receptor activator can be used to screen for a calcium receptor activation inhibitor. Although a screening method will be exemplified below, the screening method is not limited to this method.

Screening for a calcium receptor activation inhibitor can be accomplished by adding any of the peptides and amino acids described herein and a test substance to *Xenopus* oocytes or cultured cells derived from a mammal expressing the calcium receptor, measuring the intracellular electric current or intracellular calcium concentration, and choosing a compound that inhibits an increase in the intracellular electric current or calcium concentration.

The test substance used in the screening method described above may be a low molecular weight compound, saccharide, peptide, protein, and so forth.

EXAMPLES

Hereinafter, the present invention will be more specifically explained with reference to examples. However, the scope of the present invention is not limited to these examples.

Example 1

Preparation of Gene (cRNA)

The gene encoding the calcium receptor was prepared as follows. Synthetic oligo DNAs (forward primer (N) and reverse primer (C)) were prepared based on the DNA sequence registered at NCBI for the calcium receptor (NM_000388), and used for PCR (Table 1, SEQ ID NOS: 1 and 2).

TABLE 1

Synthetic oligo DNAs (forward primer (N) and reverse primer (C), h: human, r: rat)

| Code | Sequence (5'-3') |
|---|---|
| hCASR_N | ACTAATACGACTCACTATAGGGACCATGGCATTTTATAGCTGCTGCTGG |
| hCASR_C | TTATGAATTCACTACGTTTTCTGTAACAG |
| rCASR_f | ATGGAAAGCTCAGATGAAATGTC |
| rCASR_r | GGAGTGTAATACGTTTTCCGTCAC |

The primers shown in Table 1 (hCASR_N (SEQ ID NO: 1) and hCASR_C (SEQ ID NO: 2)) were synthesized from human kidney cDNA (Clontech), and PCR was performed with Pfu ultra DNA Polymerase (Stratagene) under the following conditions: After a reaction at 94° C. for 3 minutes, a cycle of reactions at 94° C. for 30 seconds, 55° C. for 30 seconds, and 72° C. for 2 minutes was repeated 35 times, and then a reaction was performed at 72° C. for 7 minutes. Whether amplification was attained by PCR was detected by agarose electrophoresis, staining with a DNA staining reagent, and ultraviolet irradiation. The length of the PCR products were confirmed by comparison with DNA markers of known sizes and simultaneously subjected to electrophoresis. The plasmid vector pBR322 (Takara) was digested with the restriction enzyme EcoRV. The gene fragment amplified by PCR was ligated to the cleavage site of the plasmid by using Ligation Kit (Promega). The *Escherichia coli* DH5α strain was transformed with each ligation reaction solution, and the transformants containing the plasmid with the PCR amplification product were cloned was selected. The PCR amplification product was confirmed by DNA sequence analysis. By using this recombinant plasmid as a template together with a cRNA preparation kit (Ambion), cRNA of the calcium receptor gene was prepared.

Example 2

Preparation of Various Samples 23 special grade amino acids were employed, including alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, ornithine, taurine (all of these from Ajinomoto), and hydroxyproline (Nakarai Tesque). Special grade amino acids were also used as D-Cys and D-Trp (Nakarai Tesque) and calcium chloride. Furthermore, the following peptide samples were used: γ-Glu-Cys-Gly (Sigma Aldrich Japan), γ-Glu-Cys(SNO)-Gly (Dojin Chemical Laboratory), γ-Glu-Ala (Bachem Feinchemikalien AG), γ-Glu-Gly (Bachem Feinchemikalien AG), γ-Glu-Cys (Sigma Aldrich Japan), γ-Glu-Met (Bachem Feinchemikalien AG), γ-Glu-Abu-Gly (Abu: α-aminobutyric acid, Bachem Feinchemikalien AG), γ-Glu-Thr (Kokusan Chemical), γ-Glu-Val (Kokusan Chemical), γ-Glu-Leu (contract manufactured product), γ-Glu-Ile (contract manufactured product), γ-Glu-Orn (Kokusan Chemical), Asp-Gly (contract manufactured product), Cys-Gly (contract manufactured product), Cys-Met (contract manufactured product), Glu-Cys (contract manufactured product), Gly-Cys (contract manufactured product), Leu-Asp (contract manufactured product), γ-Glu-Val-Val (contract manufactured product), γ-Glu-Val-Glu (contract manufactured product), γ-Glu-Val-Lys (contract manufactured product), γ-Glu-γ-Glu-Val (contract manufactured product), γ-Glu-Gly-Gly (contract manufactured product), γ-Glu-Val-Phe (contract manufactured product), γ-Glu-Val-Ser (contract manufactured product), γ-Glu-Val-Pro (contract manufactured product), γ-Glu-Val-Arg (contract manufactured product), γ-Glu-Val-Asp (contract manufactured product), γ-Glu-Val-Met (contract manufactured product), γ-Glu-Val-Thr (contract manufactured product), γ-Glu-Val-His (contract manufactured product), γ-Glu-Val-Asn (contract manufactured product), γ-Glu-Val-Gln (contract manufactured product), γ-Glu-Val-Cys (contract manufactured product), γ-Glu-Val-Orn (contract manufactured product) and γ-Glu-Ser-Gly (contract manufactured product). Glutamine and cysteine were prepared upon use, and the other samples were stored at −20° C. after preparation. Peptides having a purity of 90% or higher were used, except for γ-Glu-Cys which had a purity of 80% or higher. The pH was adjusted, as needed, to an approximately neutral pH with NaOH or HCl. The solution used for dissolution of amino acids and peptides, preparation of *Xenopus laevis* oocytes, and culture of the oocytes had the following composition: 96 mM NaCl, 2 mM KCl, 1 mM $MgCl_2$, 1.8 mM $CaCl_2$, 5 mM Hepes, pH 7.2.

Example 3

Synthesis of γ-Glu-Val-Gly

Boc-Val-OH (8.69 g, 40.0 mmol) and Gly-OBzl.HCl (8.07 g, 40.0 mmol) were dissolved in methylene chloride (100 ml), and the solution was maintained at 0° C. Triethylamine (6.13 ml, 44.0 mmol), HOBt (1-hydroxybenzotriazole, 6.74 g, 44.0 mmol), and WSC.HCl (1-ethyl-3-(3-dimethylaminopropyl)carbodiimide hydrochloride, 8.44 g, 44.0 mmol) were added to the solution, and the mixture was stirred overnight at room temperature. The reaction mixture was concentrated under reduced pressure, and the residue was dissolved in ethyl acetate (200 ml). The solution was washed with water (50 ml), 5% citric acid aqueous solution (50 ml×twice), saturated brine (50 ml), 5% sodium hydrogencarbonate aqueous solution (50 ml×twice), and saturated brine (50 ml). The organic layer was dried over anhydrous magnesium sulfate, then the magnesium sulfate was removed by filtration, and the filtrate was concentrated under reduced pressure. The residue was recrystallized from ethyl acetate/n-hexane to obtain white crystals of Boc-Val-Gly-OBzl (13.2 g, 36.2 mmol).

Boc-Val-Gly-OBzl (5.47 g, 15.0 mmol) was added to 4 N HCl/dioxane solution (40 ml), and the mixture was stirred at room temperature for 50 minutes. Dioxane was removed by concentration under reduced pressure, n-hexane (30 ml) was added to the residue, and the mixture was concentrated under reduced pressure. This procedure was repeated 3 times to quantitatively obtain H-Val-Gly-OBzl.HCl. Then, H-Val-Gly-OBzl.HCl and Z-Glu-OBzl (5.57 g, 15.0 mmol) were dissolved in methylene chloride (50 ml), and the solution was kept at 0° C. Triethylamine (2.30 ml, 16.5 mmol), HOBt (1-hydroxybenzotriazole, 2.53 g, 16.5 mmol), and WSC.HCl (1-ethyl-3-(3-dimethylaminopropyl)carbodiimide hydrochloride, 3.16 g, 16.5 mmol) were added to the solution, and the mixture was stirred at room temperature for 2 days. The reaction mixture was concentrated under reduced pressure, and the residue was dissolved in heated ethyl acetate (1500 ml). The solution was washed with water (200 ml), 5% citric acid aqueous solution (200 ml×twice), saturated brine (150 ml), 5% sodium hydrogencarbonate aqueous solution (200 ml×twice), and saturated brine (150 ml). The organic layer was dried over anhydrous magnesium sulfate, then the magnesium sulfate was removed by filtration, and the filtrate was concentrated under reduced pressure. The deposited crystals were collected by filtration, and dried under reduced pressure to obtain white crystals of Z-Glu(Val-Gly-OBzl)-OBzl (6.51 g, 10.5 mmol).

Then, Z-Glu(Val-Gly-OBzl)-OBzl (6.20 g, 10.03 mmol) was suspended in ethanol (200 ml), and 10% palladium/carbon (1.50 g) was added. A reduction reaction was performed at 55° C. for 5 hours under a hydrogen atmosphere. During the reaction, a total amount of 100 ml of water was gradually added. The catalyst was removed by filtration using a Kiriyama funnel, and the filtrate was concentrated under reduced pressure to a half volume. The reaction mixture was further filtered through a membrane filter, and the filtrate was concentrated under reduced pressure. The residue was dissolved in a small volume of water, and ethanol was added to deposit crystals, and the crystals were collected by filtration, and dried under reduced pressure to obtain a white powder of γ-Glu-Val-Gly (2.85 g, 9.40 mmol).

ESI-MS: $(M+H)^+=304.1$ $^1$H-NMR (400 MHz, $D_2O$) δ (ppm): 0.87 (3H, d, J=6.8 Hz), 0.88 (3H, d, J=6.8 Hz), 1.99-2.09 (3H, m), 2.38-2.51 (2H, m) 3.72 (1H, t, J=6.35 Hz), 3.86 (1H, d, J=17.8 Hz), 3.80 (1H, d, J=17.8 Hz), 4.07 (1H, d, J=6.8 Hz)

Example 4

Synthesis of γ-Glu-Cys(S-Me)-Gly [Cys(S-Me): S-methylcysteine]

Reduced glutathione (15.0 g, 48.8 mmol) was added to water (45 ml), and then sodium hydroxide (4.52 g, 2.2 equivalents, 107 mmol) was added little by little to the mixture while bubbled with nitrogen. Then, methyl iodide (4.56 ml, 1.5 equivalents, 73 mmol) was added to the mixture, and the mixture was sealed and stirred at room temperature for 2 hours. The reaction mixture was adjusted to pH 2 to 3 with concentrated hydrochloric acid, added with ethanol (150 ml), and stored overnight in a refrigerator. Since oily matter separated, the supernatant was removed. When the remaining oily matter was dissolved in water and ethanol was gradually added, partially crystallized oily matter was deposited. Therefore, the supernatant liquid was removed again. The residue was dissolved in water (300 ml), adsorbed onto an ion exchange resin (Dowex 1-acetate, 400 ml) applied to a column, and after washing with water, eluted with 1 N acetic acid aqueous solution. The eluate was concentrated under reduced pressure, and precipitated with water/ethanol to obtain a white powder of γ-Glu-Cys(S-Me)-Gly (5.08 g, 15.8 mmol).

FAB-MS: $(M+H)^+=322$.

$^1$H-NMR (400 MHz, $D_2O$) δ (ppm): 2.14 (3H, s), 2.15-2.22 (2H, m), 2.50-2.58 (2H, m), 2.86 (1H, dd, J=9.0 Hz, J=14.0 Hz), 3.03 (1H, dd, J=5.0 Hz, J=14.0 Hz), 3.84 (1H, t, J=6.5 Hz), 3.99 (2H, S), 4.59 (1H, dd, J=5.0 Hz, J=9.0 Hz).

Example 5

Synthesis of Other Peptides

γ-Glu-Met(O), γ-Glu-Val-$NH_2$, γ-Glu-Val-ol, γ-Glu-Ser, γ-Glu-Tau, γ-Glu-Cys(S-Me)(O), γ-Glu-t-Leu, γ-Glu-Cys(S-allyl)-Gly, and γ-Glu-Cys(S-Me) were synthesized in a manner similar to that described in Examples 3 and 4.

Example 6

Evaluation of Calcium Receptor Activation Activity

To evaluate calcium receptor activation activity, a Ca ion concentration-dependent Cl ionic current measuring method using a *Xenopus laevis* oocyte expression system was used. If each activator is added to *Xenopus laevis* oocytes expressing the calcium receptor, intracellular Ca ions increase. Then, the Ca ion concentration-dependent Cl channel opens, and the intracellular current value changes as an ionic current. By measuring the change in this intracellular current value, the presence or absence of calcium receptor activation activity can be determined.

Specifically, the abdomen of *Xenopus laevis* was opened, and an egg batch was taken out and treated with a 1% collagenase solution at 20° C. for 2 hours to obtain individual oocytes. Into the oocytes, 50 nl of 1 μg/μl receptor cRNA or 50 nl of sterilized water per oocyte was introduced by using a micro glass capillary, and the oocytes were cultured at 18° C. for 2 or 3 days. For the culture, a solution obtained by adding 2 mM pyruvic acid, 10 U/ml of penicillin, and 10 μg/ml of streptomycin to the solution in Example 2 was used. After the culture, a test solution was added to the oocytes containing either the cRNA or sterilized water. Electrophysiological measurement was performed by using an amplifier, Geneclamp500 (Axon), and recording software, AxoScope 9.0 (Axon). The oocytes were voltage-clamped at −70 mV by the double electrode voltage clamp method, and the intracellular current was measured via the Ca ion concentration-dependent Cl ion channel. The maximum value of the intracellular current was considered as the response current value.

Example 7

Evaluation of Calcium Receptor Activation Activity of Calcium

The calcium receptor activation activity of calcium was evaluated by using the method described in Example 6. That is, oocytes containing either cRNA of the calcium receptor or sterilized water were prepared, and voltage-clamped at −70 mV by the double electrode voltage clamp method. To the voltage-clamped oocytes, calcium was added (2 mM, 5 mM, 10 mM, 20 mM), and Ca ion concentration-dependent Cl response current was measured. The results are shown in FIG. 1. From these results, it was confirmed that the cRNA of the calcium receptor was functionally expressed in the oocytes. Furthermore, since the oocytes containing water did not respond to even high concentration calcium, it was confirmed that the calcium receptor is not expressed in the oocytes.

Example 8

Evaluation of Calcium Receptor Activation Activity of L-Amino Acids

Figure 2:
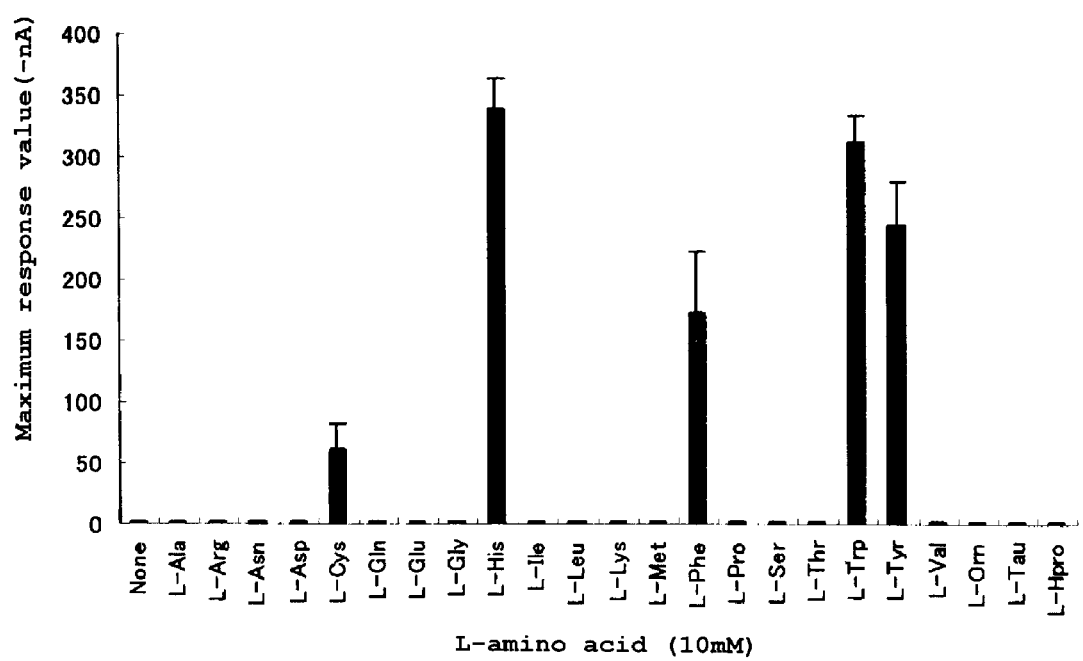
FIG. 2 shows the action of L-amino acids on the calcium receptor. The human calcium receptor cRNA was introduced into *Xenopus laevis* oocytes by microinjection. Values of intracellular response currents were recorded when a 10 mM L-amino acid solution was added. The maximum values of intracellular currents were considered response current values. It was confirmed that no response was observed in control oocytes microinjected with distilled water.

Calcium receptor activation activity of L-amino acids was evaluated by using the method described in Example 6. That is, oocytes containing either cRNA of the calcium receptor or sterilized water were prepared, and voltage-clamped at −70 mV by the double electrode voltage clamp method. To the voltage-clamped oocytes, alanine (10 mM), arginine (10 mM), asparagine (10 mM), aspartic acid (10 mM), cysteine (10 mM), glutamine (10 mM), glutamic acid (10 mM), glycine (10 mM), histidine (10 mM), isoleucine (10 mM), leucine (10 mM), lysine (10 mM), methionine (10 mM), phenylalanine (10 mM), proline (10 mM), serine (10 mM), threonine (10 mM), tryptophan (10 mM), tyrosine (10 mM), valine (10 mM), ornithine (10 mM), taurine (10 mM), or hydroxyproline (10 mM) was added, and Ca ion concentration-dependent Cl response current was measured. The results are shown in FIG. 2. By these results, it was demonstrated that cysteine, histidine, phenylalanine, tryptophan, and tyrosine had definite calcium receptor activation activity. As for the aforementioned amino acids, the activation activity was reported in Proc. Natl. Acad. Sci. USA, 2000 Apr. 25, 97(9):4814-9.

Example 9

Evaluation of Calcium Receptor Activation Activity of D-Cysteine

Figure 3:
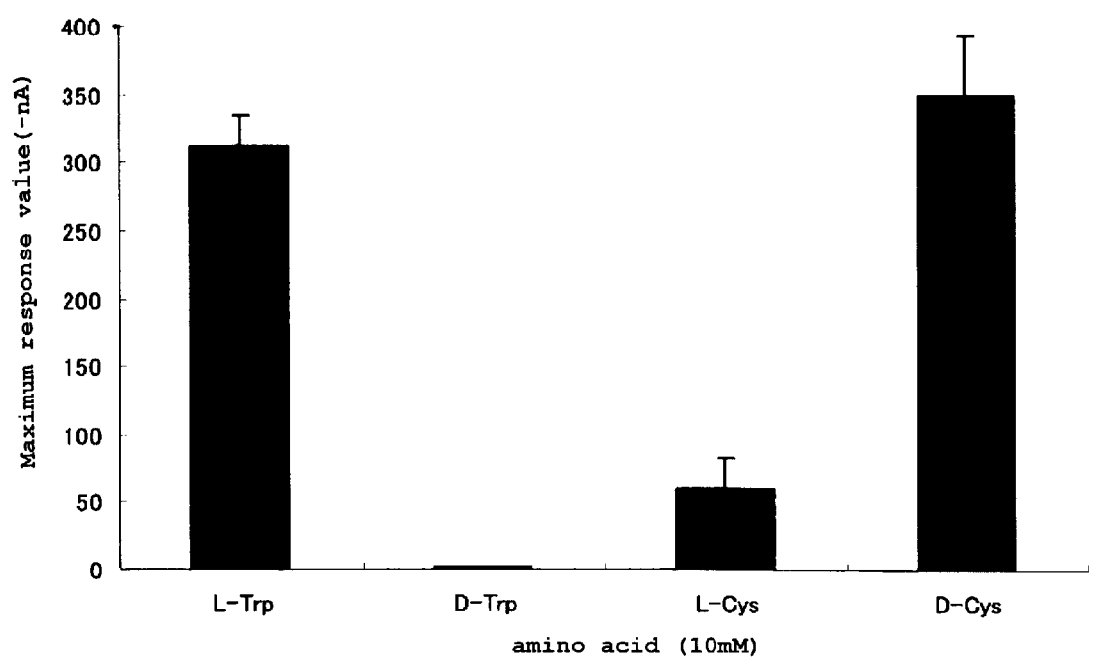
FIG. 3 shows the action of D-amino acids on the calcium receptor. The human calcium receptor cRNA was introduced into *Xenopus laevis* oocytes by microinjection. Values of intracellular response currents were recorded when a 10 mM D-amino acid solution was added. The maximum values of intracellular currents were considered response current values. It was confirmed that no response was observed in control oocytes microinjected with distilled water.

Calcium receptor activation activity of D-cysteine was evaluated by using the method described in Example 6. That is, oocytes containing either cRNA of the calcium receptor or sterilized water were prepared, and voltage-clamped at −70 mV by the double electrode voltage clamp method. To the voltage-clamped oocytes, D-cysteine (10 mM), L-cysteine (10 mM), D-tryptophan (10 mM), or L-tryptophan (10 mM) was added, and Ca ion concentration-dependent Cl response current was measured. The results are shown in FIG. 3. By these results, it was demonstrated that D-cysteine had definitive calcium receptor activation activity.

Example 10

Evaluation of Calcium Receptor Activation Activity of Peptides

Figure 4:
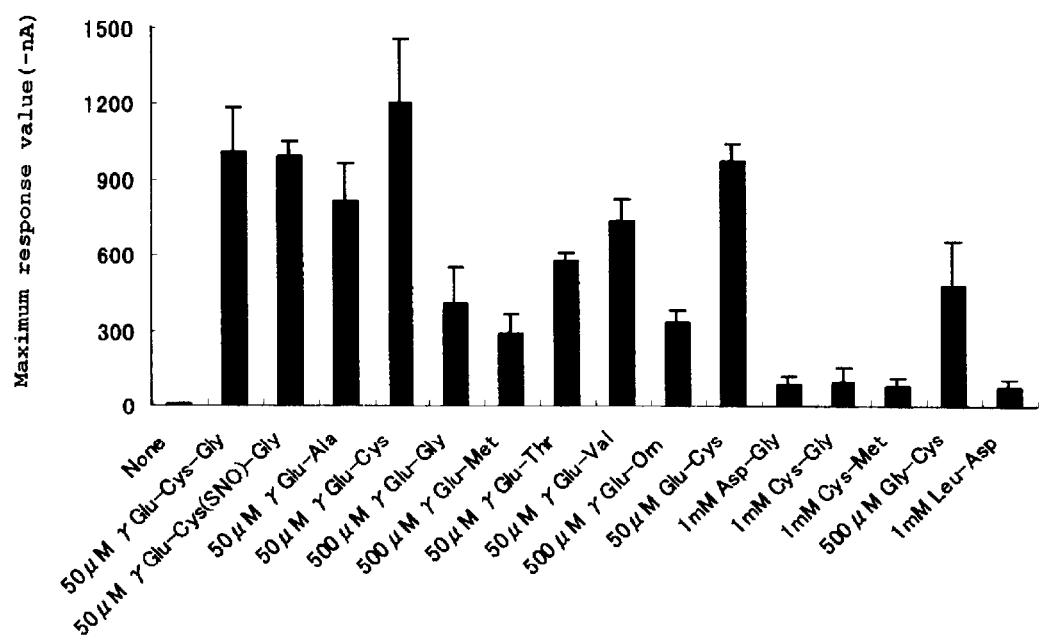
FIG. 4 shows the action of peptides on the calcium receptor. The human calcium receptor cRNA was introduced into *Xenopus laevis* oocytes by microinjection. Values of intracellular response currents were recorded when a peptide solution was added at an arbitrary concentration. The maximum values of intracellular currents were considered response current values. It was confirmed that no response was observed in control oocytes microinjected with distilled water.

Calcium receptor activation activity of peptides was evaluated by using the method described in Example 6. That is, oocytes containing either cRNA of the calcium receptor or sterilized water were prepared, and voltage-clamped at −70 mV by the double electrode voltage clamp method. To the voltage-clamped oocytes, γ-Glu-Cys-Gly (50 μM), γ-Glu-Cys(SNO)-Gly (50 μM), γ-Glu-Ala (50 μM), γ-Glu-Gly (500 μM), γ-Glu-Cys (50 μM), γ-Glu-Met (500 μM), γ-Glu-Thr (50 μM), γ-Glu-Val (50 μM), γ-Glu-Orn (500 μM), Asp-Gly (1 mM), Cys-Gly (1 mM), Cys-Met (1 mM), Glu-Cys (50 μM), Gly-Cys (500 μM) or Leu-Asp (1 mM) was added, and Ca ion concentration-dependent Cl response current was measured. The results are shown in FIG. 4. By these results, it was demonstrated that the aforementioned peptides had definitive calcium receptor activation activity.

Example 11

Evaluation of Calcium Receptor Activation Activity of Peptides

Calcium receptor activation activity of peptides was evaluated in the same manner as that of Example 10. Each of the peptides shown in Table 2 was added to voltage-clamped oocytes at 1000 μM, 300 μM, 100 μM, 30 μM, 10 μM, 3 μM, 1 μM, 0.3 μM, and 0.1 μM, and Ca ion concentration-dependent Cl response current was measured. The lowest concentration for which current was detected was shown in Table 2 as the activity. From these results, it became clear that these 32 peptides had calcium receptor activation activity.

TABLE 2

| No. | Peptide | Activity |
| --- | --- | --- |
| 1 | γ-Glu-Met(O) | 1000 μM |
| 2 | γ-Glu-Val-Val | 1000 μM |
| 3 | γ-Glu-Val-Glu | 1000 μM |
| 4 | γ-Glu-Val-Lys | 1000 μM |

TABLE 2-continued

| No. | Peptide | Activity |
| --- | --- | --- |
| 5 | γ-Glu-Val-Arg | 1000 μM |
| 6 | γ-Glu-Val-Asp | 1000 μM |
| 7 | γ-Glu-Val-Met | 1000 μM |
| 8 | γ-Glu-Val-Thr | 1000 μM |
| 9 | γ-Glu-γ-Glu-Val | 1000 μM |
| 10 | γ-Glu-Val-NH2 | 1000 μM |
| 11 | γ-Glu-Val-ol | 1000 μM |
| 12 | γ-Glu-Ser | 300 μM |
| 13 | γ-Glu-Tau | 300 μM |
| 14 | γ-Glu-Cys(S-Me)(O) | 300 μM |
| 15 | γ-Glu-Val-His | 100 μM |
| 16 | γ-Glu-Val-Orn | 100 μM |
| 17 | γ-Glu-Leu | 100 μM |
| 18 | γ-Glu-Ile | 100 μM |
| 19 | γ-Glu-t-Leu | 100 μM |
| 20 | γ-Glu-Cys(S-allyl)-Gly | 100 μM |
| 21 | γ-Glu-Val-Asn | 30 μM |
| 22 | γ-Glu-Gly-Gly | 30 μM |
| 23 | γ-Glu-Val-Phe | 30 μM |
| 24 | γ-Glu-Val-Ser | 30 μM |
| 25 | γ-Glu-Val-Pro | 30 μM |
| 26 | γ-Glu-Ser-Gly | 30 μM |
| 27 | γ-Glu-Cys(S-Me) | 30 μM |
| 28 | γ-Glu-Val-Cys | 10 μM |
| 29 | γ-Glu-Val-Gln | 10 μM |
| 30 | γ-Glu-Abu-Gly | 3 μM |
| 31 | γ-Glu-Cys(S-Me)-Gly | 3 μM |
| 32 | γ-Glu-Val-Gly | 0.1 μM |

Example 12

Distribution of the Calcium Receptor in a Living Body

In order to determine the distribution of the calcium receptor in a living body, expression of the calcium receptor in tissues was investigated using RNAs obtained from rats in the quantitative RT-PCR method.

RNAs were prepared from rat tissues as follows. From 15-week old male F344 rats, tissue was isolated from the cerebrum, cerebellum, lung, heart, liver, kidney, adrenal body, thyroid, parathyroid, pancreas, spleen, esophagus, upper third of stomach, fundus of stomach, duodenum, jejunum, ileum, caecum, colon, rectum, testis, epididymis, bladder, bone marrow, gastrocnemial muscle, soleus, skeletal muscle, fat, prostate, tongue, sublingual gland, and thymus. Total RNA was prepared by using Isogen (Nippon Gene). Each tissue was homogenized by using a Fast Prep (BIO101) or Polytron homogenizer, and total RNA was extracted from the homogenate. By using the total RNA as a template, oligo dT primers, and Superscript III reverse transcriptase (Invitrogen), cDNA was synthesized. The primers shown in Table 1 (rCASR_f: SEQ ID NO: 3 and rCASR_r: SEQ ID NO: 4) were synthesized, and RT-PCR of the calcium receptor was performed as follows. By quantitative PCR using cDNA of each tissue as a template, SYBR Green Realtime PCR Master Mix (TOYOBO), and ABI PRISM 7700 Sequence Detector, the expression amount of the calcium receptor gene was analyzed. Distribution of tissue expression is shown in Table 3. Only for pancreas, human total RNA (Stratagene) was used.

From these results, it was confirmed that the calcium receptor was widely expressed throughout the body, and not only in the parathyroid and kidney. This suggested that the calcium receptor was involved not only in functions of the parathyroid and kidney but also in various physiological functions of peripheral tissues and peripheral organs.

TABLE 3

Distribution of calcium receptor in the body

| CaSR | |
|---|---|
| Cerebrum | o |
| Cerebellum | o |
| Lung | x |
| Heart | o |
| Liver | o |
| Kidney | o |
| Adrenal body | x |
| Thyroid | o |
| Pancreas | o |
| Spleen | o |
| Esophagus | o |
| Upper of stomach | o |
| Fundus of stomach | o |
| Duodenum | o |
| Jejunum | o |
| Ileum | o |
| Caecum | o |
| Colon | o |
| Rectum | o |
| Testis | o |
| Epididymis | o |
| Bladder | x |
| Bone marrow | o |
| Gastrocnemial muscle | o |
| Soleus | o |
| Skeletal muscle | o |
| Fat | o |
| Prostate | x |
| Tongue | o |
| Sublingual gland | o |
| Thymus | o |
| Aorta | o |

Example 13

Pharmacological Evaluation of Calcium Receptor Activators Using Animals

The pharmacological effects of the peptides were confirmed by animal study. Parathyroid hormone (PTH) is one of the major proteins which relate to calcium homeostasis. Increase in PTH is directly responsible for hyperparathyroidism and hypoparathyroidism. It is known that PTH is secreted from the parathyroid gland, and its secretion is inhibited when the calcium receptor is activated. Male, 10 weeks old, Sprague-Dawley strain rats were used. "Rat Intact PTH ELISA KIT" (Immutopics) was used for measuring PTH according to the manufacturer's recommended protocol. 100 mg/ml of γ-Glu-Val-Gly was dissolved in physiological saline, and 0.1 ml/100 g body weight for each was injected through the tail vein. Blood was collected from the vein under the right clavicle, and blood serum was obtained by centrifugation. Each group consists of 3 rats, and PTH variation is shown below as average value±standard error. The result for the peptide-administered group was: 148±72.5 pg/ml before the administration and 9.44±2.94 pg/ml 15 minutes after the administration; meanwhile, the result for the control group (physiological saline administered group) was: 89.4±49.5 pg/ml before the administration and 41.1±11.6 pg/ml 15 minutes after the administration. As a result, PTH levels decreased as a result of the administration of the peptides.

INDUSTRIAL APPLICABILITY

Receptor activators for the GPCR (G-protein coupling type receptor) are universally applicable as curative agents of various diseases. Examples of curative commercial agents so far, or those under research, include the acetylcholine receptor activator (for treating Alzheimer disease), the adrenoreceptor activator (for treating bronchial asthma, for treating obesity), the opioid receptor activator (for treating pain diseases), the receptor activator (for treating pain diseases), the calcitonin receptor activator (for treating osteoporosis), the cholecystokinin receptor activator (for treating diabetes), the serotonine receptor activator (for treating migraine), the dopamine receptor activator (for treating Parkinson's disease, sedative), the melatonin receptor activator (for treating primary insomnia), the melanocortin receptor activator (for treating obesity), and so forth.

As for the range of applications of the calcium receptor activator as a curative agent, since the calcium receptor is distributed over a wide range of tissues as shown in Example 12, Table 3, it is expected to be applicable to a wide range of diseases.

While the invention has been described in detail with reference to preferred embodiments thereof, it will be apparent to one skilled in the art that various changes can be made, and equivalents employed, without departing from the scope of the invention. All the cited references herein are incorporated as a part of this application by reference.

The invention claimed is:

1. A method of activating a calcium receptor, comprising contacting a cell expressing the calcium receptor with a substance selected from the group consisting of γ-Glu-Ala, γ-Glu-Gly, γ-Glu-Cys, γ-Glu-Met, γ-Glu-Thr, γ-Glu-Val, γ-Glu-Orn, Asp-Gly, Cys-Gly, Cys-Met, Glu-Cys, Gly-Cys, Leu-Asp, D-Cys, γ-Glu-Met(O), γ-Glu-Val-NH$_2$, γ-Glu-Val-ol, γ-Glu-Ser, γ-Glu-Tau, γ-Glu-Cys(S-Me)(O), γ-Glu-Leu, γ-Glu-Ile, γ-Glu-t-Leu, γ-Glu-Cys(S-Me), and combinations thereof.

2. The method of claim 1, wherein said cell is present in culture and is selected from the group consisting of *Xenopus laevis* oocytes, hamster ovarian cells, and human fetal kidney cells.

3. A method of activating a calcium receptor in an animal in need thereof comprising administering a substance to said animal for a time and under conditions effective to activate a calcium receptor, wherein said substance is selected from the group consisting of γ-Glu-Ala, γ-Glu-Gly, γ-Glu-Cys, γ-Glu-Met, γ-Glu-Thr, γ-Glu-Val, γ-Glu-Orn, Asp-Gly, Cys-Gly, Cys-Met, Glu-Cys, Gly-Cys, Leu-Asp, D-Cys, γ-Glu-Met(O), γ-Glu-Val-NH$_2$, γ-Glu-Val-ol, γ-Glu-Ser, γ-Glu-Tau, γ-Glu-Cys(S-Me)(O), γ-Glu-Leu, γ-Glu-Ile, γ-Glu-t-Leu, γ-Glu-Cys(S-Me), and combinations thereof.

4. A method of activating a calcium receptor in an animal in need thereof comprising administering a composition to said animal for a time and under conditions effective to activate a calcium receptor, wherein said composition comprises a pharmaceutical carrier and a substance selected from the group consisting of γ-Glu-Ala, γ-Glu-Gly, γ-Glu-Cys, γ-Glu-Met, γ-Glu-Thr, γ-Glu-Val, γ-Glu-Orn, Asp-Gly, Cys-Gly, Cys-Met, Glu-Cys, Gly-Cys, Leu-Asp, D-Cys, γ-Glu-Met(O), γ-Glu-Val-NH$_2$, γ-Glu-Val-ol, γ-Glu-Ser, γ-Glu-Tau, γ-Glu-Cys(S-Me)(O), γ-Glu-Leu, γ-Glu-Ile, γ-Glu-t-Leu, γ-Glu-Cys(S-Me), and combinations thereof.

* * * * *